US011473054B2

(12) United States Patent
Matsusaki

(10) Patent No.: US 11,473,054 B2
(45) Date of Patent: Oct. 18, 2022

(54) METHOD OF PRODUCING THREE-DIMENSIONAL TISSUE HAVING VASCULAR SYSTEM STRUCTURE, AND THREE-DIMENSIONAL TISSUE INCLUDING GEL HAVING VASCULAR SYSTEM STRUCTURE

(71) Applicant: OSAKA UNIVERSITY, Suita (JP)

(72) Inventor: Michiya Matsusaki, Suita (JP)

(73) Assignee: OSAKA UNIVERSITY, Suita (JP)

( * ) Notice: Subject to any disclaimer, the term of this patent is extended or adjusted under 35 U.S.C. 154(b) by 419 days.

(21) Appl. No.: 15/998,571

(22) PCT Filed: Jan. 31, 2017

(86) PCT No.: PCT/JP2017/003368
§ 371 (c)(1),
(2) Date: Aug. 15, 2018

(87) PCT Pub. No.: WO2017/141691
PCT Pub. Date: Aug. 24, 2017

(65) Prior Publication Data
US 2019/0093070 A1 Mar. 28, 2019

(30) Foreign Application Priority Data
Feb. 16, 2016 (JP) .............................. JP2016-027196

(51) Int. Cl.
*C12N 5/00* (2006.01)
*A61L 27/22* (2006.01)
*A61L 27/38* (2006.01)
*A61L 27/50* (2006.01)
*C12N 5/077* (2010.01)
*C12N 5/071* (2010.01)

(52) U.S. Cl.
CPC .......... *C12N 5/0062* (2013.01); *A61L 27/222* (2013.01); *A61L 27/3826* (2013.01); *A61L 27/507* (2013.01); *C12N 5/00* (2013.01); *C12N 5/069* (2013.01); *C12N 5/0652* (2013.01); *A61F 2240/002* (2013.01); *A61L 2430/34* (2013.01)

(58) Field of Classification Search
None
See application file for complete search history.

(56) References Cited

U.S. PATENT DOCUMENTS

| 10,117,968 | B2 | 11/2018 | Lewis et al. | |
|---|---|---|---|---|
| 2008/0261306 | A1 | 10/2008 | Neumann | |
| 2012/0089238 | A1* | 4/2012 | Kang | A61L 27/26 623/23.72 |
| 2015/0376595 | A1 | 12/2015 | Leduc et al. | |
| 2016/0287756 | A1 | 10/2016 | Lewis et al. | |

FOREIGN PATENT DOCUMENTS

| JP | 2012-115254 A | 6/2012 |
|---|---|---|
| JP | 2014-236698 A | 12/2014 |
| JP | 2015-100334 A | 6/2015 |
| WO | WO 2014/030418 A1 | 2/2014 |
| WO | WO 2015/069619 A1 | 5/2015 |
| WO | WO 2017/019422 A1 | 2/2017 |

OTHER PUBLICATIONS

Planat-Bernard et al., Circulation 2004; vol. 109: 656-663 (Year: 2004).*
Cheuh et al., Biomed Microdevices, Feb. 2010; 12(1): 145-151 (Year: 2010).*
Ito et al., J Mater Sci: Mater Med (2012) 23: 1291-1297 (Year: 2012).*
Lumen, Cardiovascular Systems: Blood Vessels, retrieved from the internet Oct. 14, 2020: https://courses.lumenlearning.com/boundless-ap/chapter/blood-vessel-structure-and-function/(Year: 2020).*
Wanjare et al., Biotechnol J. Apr. 2013; 8(4): 434-447 (Year: 2013).*
Hitchcock et al Ann N.Y. Acad. Sci. 1131: 44-49 (2008) (Year: 2008).*
The Lymphoid System, Pearson Education 2012 (Year: 2012).*
Banfi et al., Clin Chem Lab Med 2007; 45(5): 565-576 (Year: 2007).*
Chemistry Master, Diprotic and Polyprotic Acids, retrieved from the internet (2021): https://courses.lumenlearning.com/trident-boundless-chemistry/chapter/diprotic-and-polyprotic-acids/ (Year: 2021).*
Overview of Acids and Bases, Chem Libretext, retrieved from the internet (2021): https://chem.libretexts.org/Bookshelves/Physical_and_Theoretical_Chemistry_Textbook_Maps/Supplemental_Modules_(Physical_and_Theoretical_Chemistry)/Acids_and_Bases/Acid/Overview_of_Acids_and_Bases (Year: 2021).*
Acids and Bases and the pH Scale, nau.edu, retrieved from the internet (2021): https://www2.nau.edu/lrm22/lessons/acids_and_bases/acids_and_bases.html#:~:text=If%20there%20are%20more%20positively,then%20the%20substance%20becomes%20basic. (Year: 2021).*

(Continued)

*Primary Examiner* — Evelyn Y Pyla
(74) *Attorney, Agent, or Firm* — Oblon, McClelland, Maier & Neustadt, L.L.P.

(57) ABSTRACT

Provided is a method for producing a three-dimensional tissue having a vascular system structure, said method comprising: (a) a step for forming a vascular system structure template using a gel; (b) a step for forming a three-dimensional tissue in the vicinity of the template; (c) a step for dissolving the template using a cationic solution; and (d) a step for seeding vascular endothelial cells and/or lymphatic vessel endothelial cells in a void remaining after the dissolution of the template. Also provided is a method for producing a three-dimensional tissue having a vascular system structure, said method comprising: (i) a step for forming a vascular system structure template using a gel; (ii) a step for seeding vascular endothelial cells and/or lymphatic vessel endothelial cells on the template; (iii) a step for forming a three-dimensional tissue in the vicinity of the cells seeded above; and (iv) a step for dissolving the template using a cationic solution. Also provided is a three-dimensional tissue comprising a gel which has a vascular system structure.

13 Claims, 5 Drawing Sheets

(56) References Cited

OTHER PUBLICATIONS

International Search Report dated Apr. 4, 2017 in PCT/JP2017/003368, 2 pages.
International Preliminary Report on Patentability and Written Opinion dated Aug. 21, 2018 in PCT/JP2017/003368 (English Translation only), 6 pages.
Jordan S. Miller et al., "Rapid Casting of Patterned Vascular Networks for Perfusable Engineered Three-Dimensional Tissues", Nature Materials, vol. 11, No. 9, Sep. 2012, pp. 768-774.
Katsuhisa Sakaguchi et al., "In Vitro Engineering of Vascularized Tissue Surrogates", Scientific Reports, vol. 3, Article No. 1316, 2013, pp. 1-7.
Xue-Ying Wang et al., "Engineering Interconnected 3D Vascular Networks in Hydrogels Using Molded Sodium Alginate Lattice as the Sacrificial Template", Lab on a Chip, vol. 14, 2014, pp. 2709-2716 and Cover Pages.
Yamada, Sodai, et al., "Preparation of High-Dispersion Cell Solution via Ion-Crosslinking between Double Helix Polymer Chains and Their Application for Inkjet Cell Printing", The 95th Annual Meeting of The Chemical Society of Japan in Spring, 2015, Koen Yokoshu III, p. 874, 1 J5-33 and Cover Pages.
Michiya Matsusaki et al., "The Construction of 3D-engineered Tissues Composed of Cells and Extracellular Matrices by Hydrogel Template Approach", Biomaterials, vol. 28, Issue 17, 2007, pp. 2729-2737.
Extended European Search Report dated Jun. 24, 2019 in Patent Application No. 17752954.2, 7 pages.
Madden, L. R. et al., "Proangiogenic scaffolds as functional templates for cardiac tissue engineering", Proceeds of the National Academy of Sciences, XP055083964, vol. 107, No. 34, Aug. 24, 2010, pp. 15211-15216.
Matsusaki, M. et al., "Fabrication of Perfusable Pseudo Blood Vessels by Controlling Sol-Gel Transition of Gellan Gum Templates", ACS Biomaterials Science & Engineering, XP055594463, Apr. 12, 2019, 7 pages.
Liu, C. Y. et al., "Control of vascular network location in millimeter-sized 3D-tissues by micrometer-sized collagen coated cells", Biochemical and Biophysical Research Communications, XP029445499, vol. 472, No. 1, Feb. 23, 2016, pp. 131-136.
Chong et al., "Development of cell-selective films for layered co-culturing of vascular progenitor cells", Biomaterials, vol. 30, No. 12, Apr. 1, 2009, pp. 2241-2251, XP025990548.
El-Sherbiny et al., "Hydrogel scaffolds for tissue engineering: Progress and challenges", Global Cardiology Science & Practice, vol. 2013, No. 3, Sep. 1, 2013, 27 pages, XP055441085.
Office Action dated Oct. 14, 2021 in European Patent Application No. 17 752 954.2, 4 pages.

* cited by examiner

[Fig. 1]
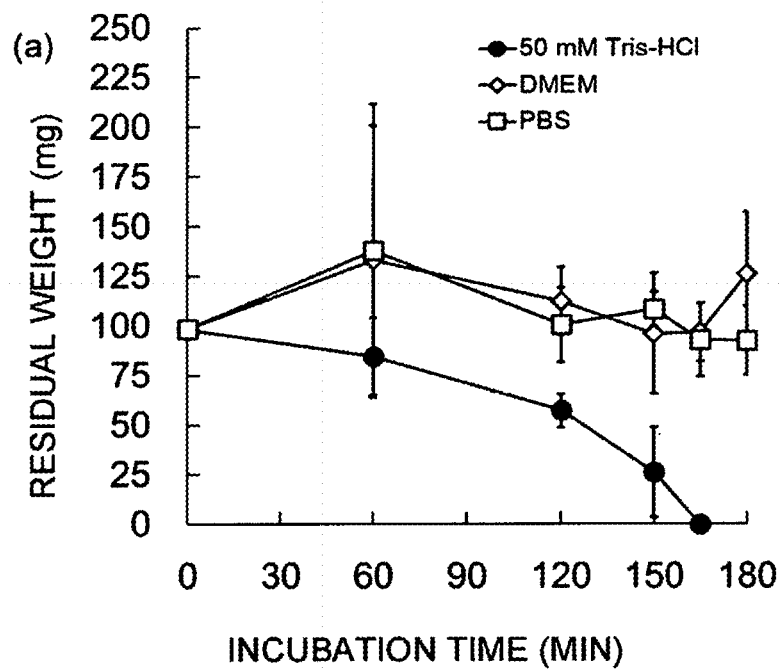
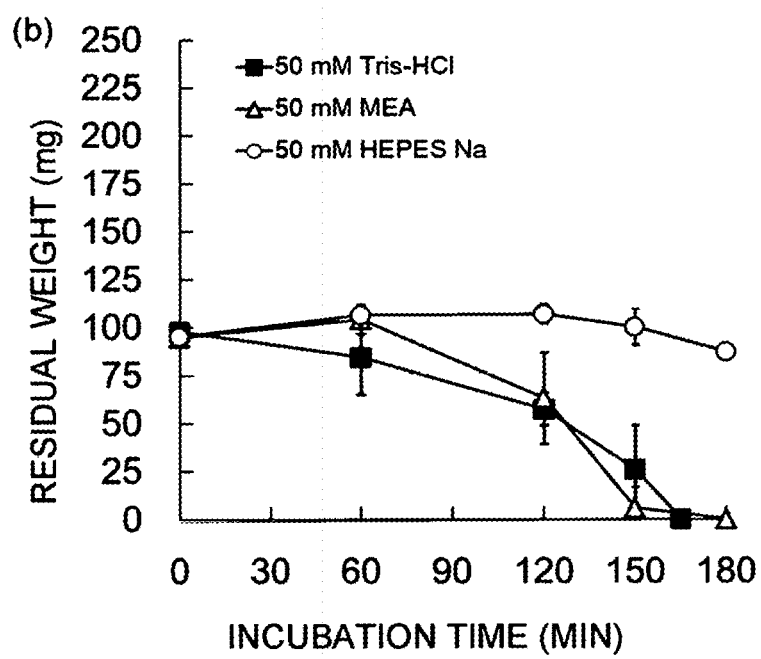

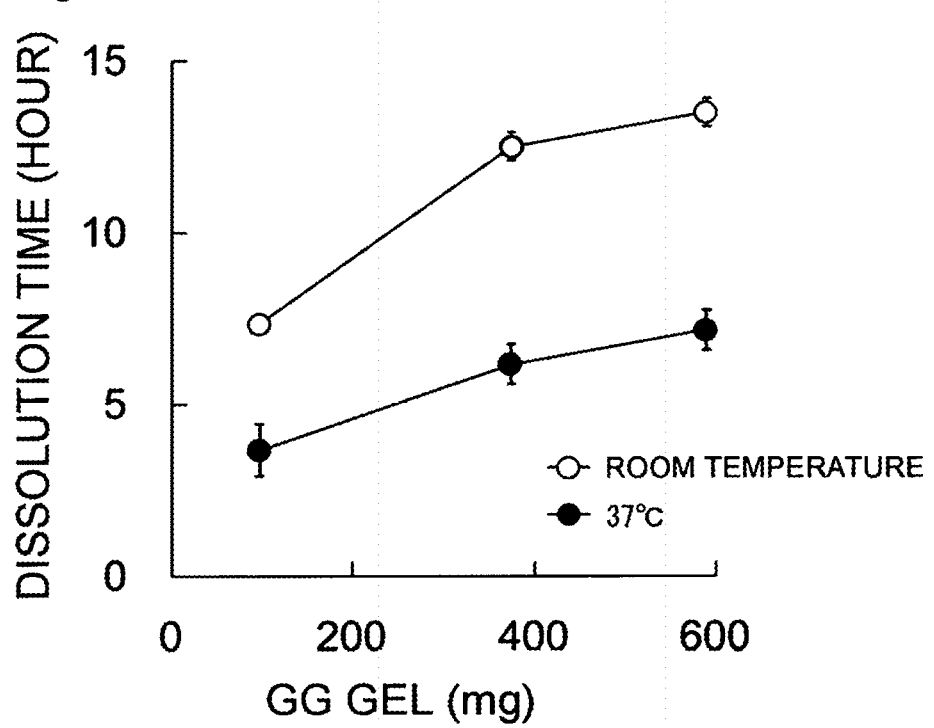
[Fig. 2]

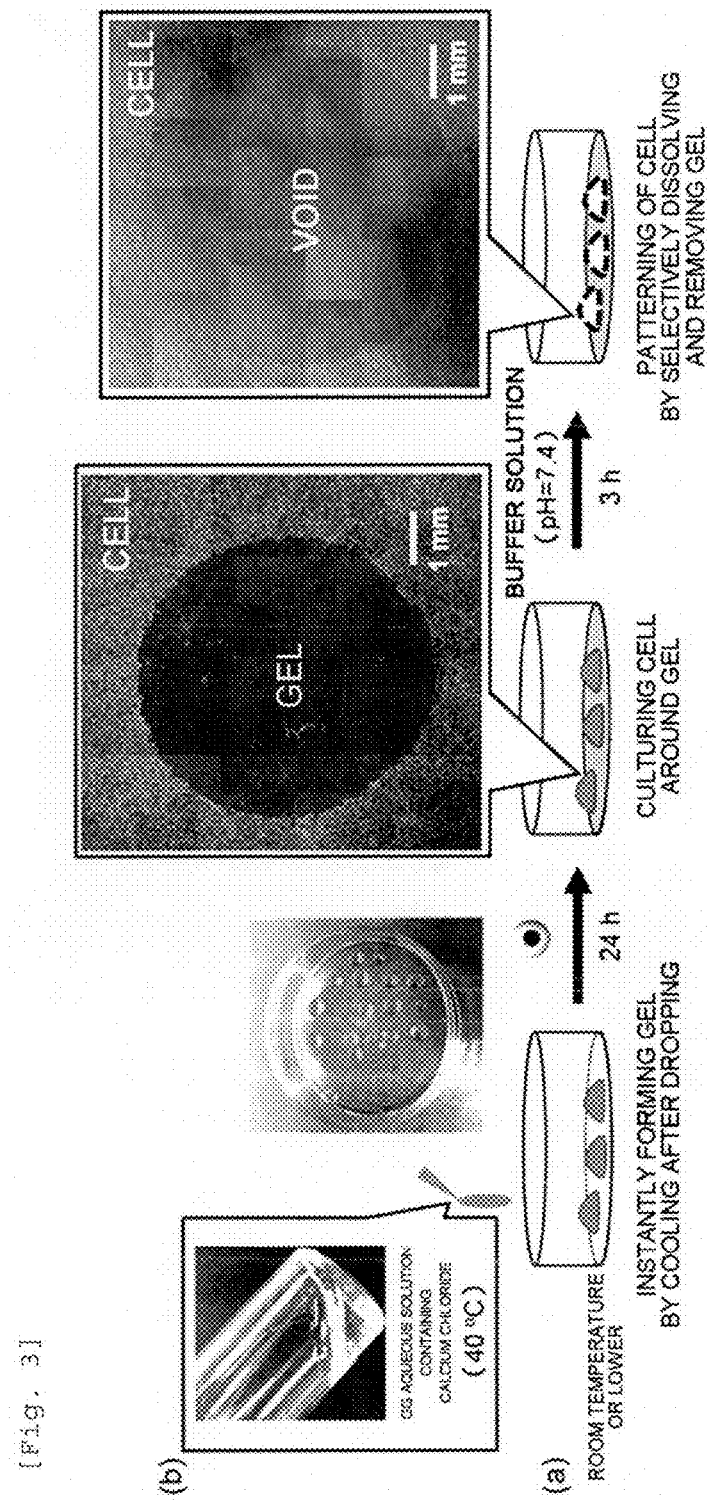

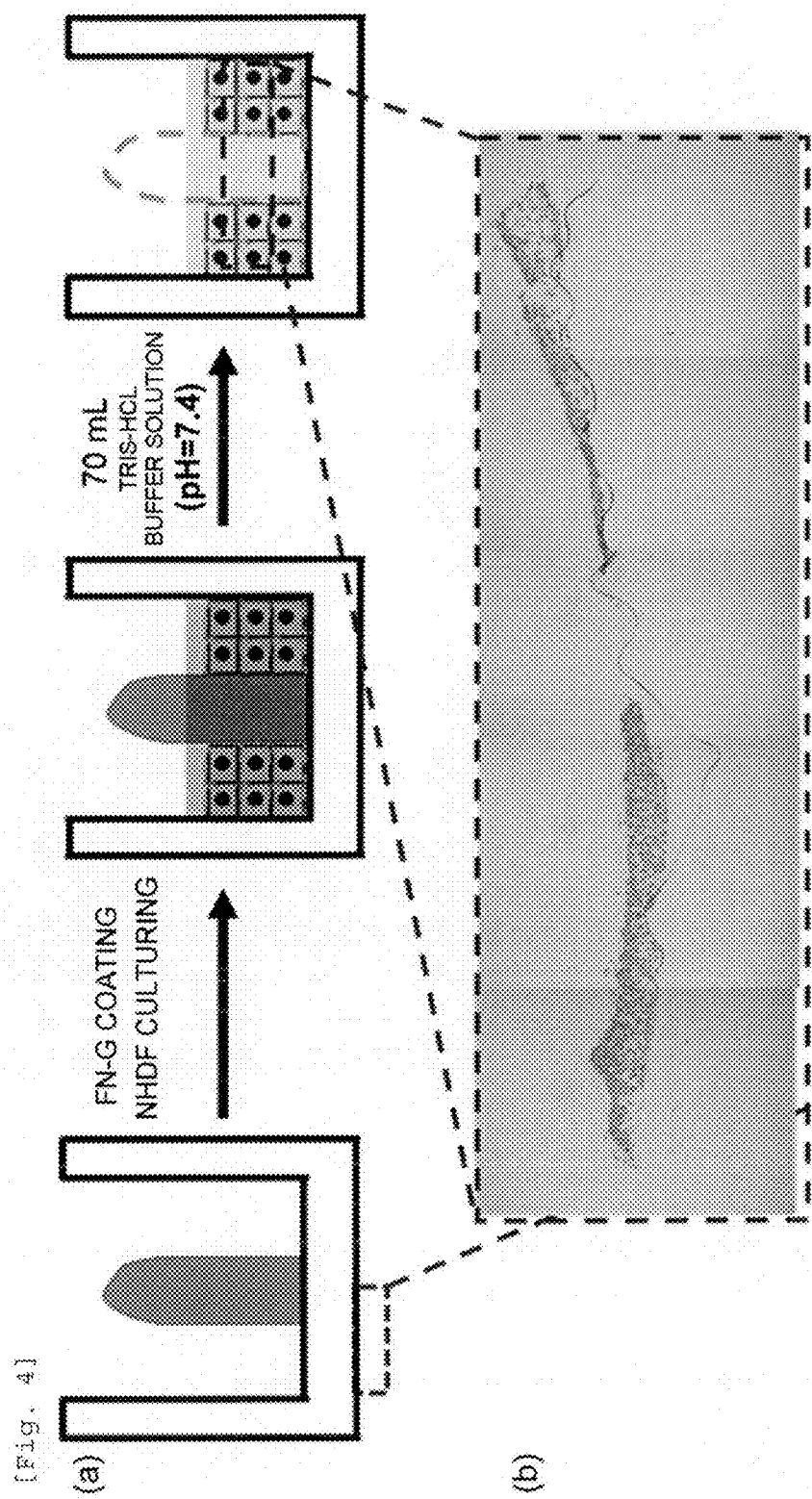

[Fig. 5]
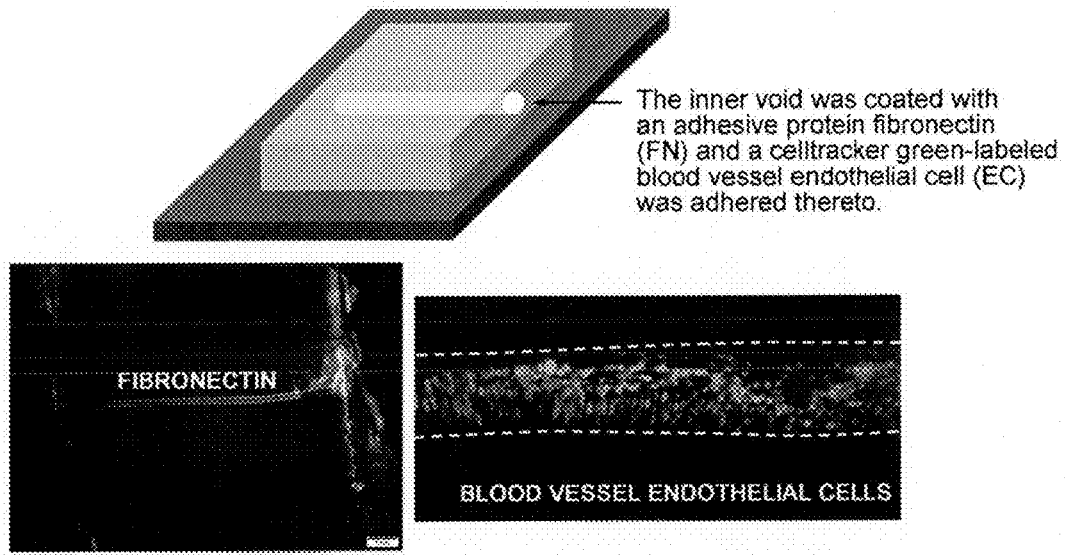
[Fig. 6]
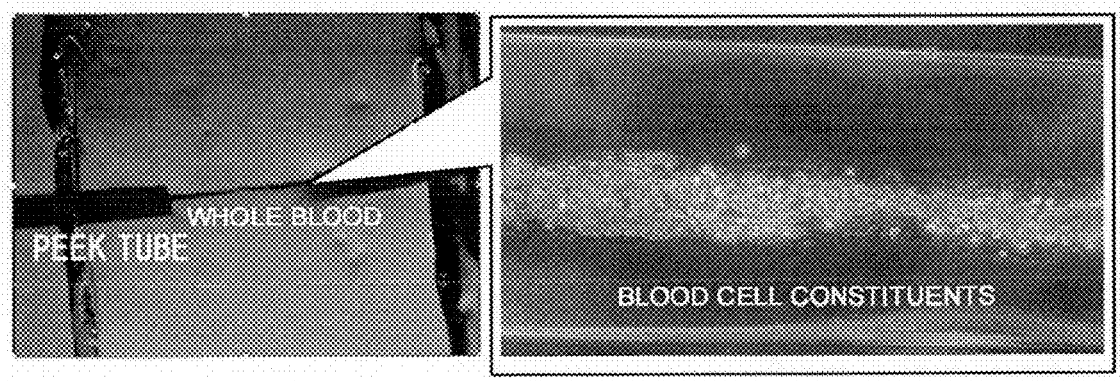

METHOD OF PRODUCING THREE-DIMENSIONAL TISSUE HAVING VASCULAR SYSTEM STRUCTURE, AND THREE-DIMENSIONAL TISSUE INCLUDING GEL HAVING VASCULAR SYSTEM STRUCTURE

TECHNICAL FIELD

The present invention relates to a method of producing a three-dimensional tissue having a vascular system structure. The present invention also relates to a three-dimensional tissue including gel having a vascular system structure and a method of producing the same.

BACKGROUND ART

Recently, various techniques have been developed for constructing a three-dimensional tissue of cells in vitro. The three-dimensional tissue constructed by such techniques is expected to be used as a graft in regenerative medicine. Further, it is also expected to be used for assessing a drug response or the like in development of pharmaceuticals. However, there is a problem that the three-dimensional tissue itself cannot survive without a blood vessel network in its inside. Further, in case that where the assessment of drug response or the like is performed using the three-dimensional tissue without a blood vessel network or with only a blood vessel network that has no connection to the outside, a drug fails to enter the blood vessel network or diffuses over the three-dimensional tissue by simple diffusion. This makes it difficult to accurately observe an effect of the drug.

Patent literature 1 discloses a method of producing a three-dimensional structure body of cells by culturing coated cells on a substrate, where the entire surfaces of the cells are coated with adhesive films. Further, Patent literature 1 discloses that a blood vessel network can be formed in the three-dimensional structure body by using a blood vessel endothelial cell. However, because the blood vessel network in Patent literature 1 is formed by self-organization of the cells as a driving force, it is difficult to control a three-dimensional configuration of the blood vessel network.

Non-patent literature 1 discloses a method of constructing a three-dimensional tissue having a blood vessel network by producing a lattice fiber using vitrified sugar, producing gel of collagen or the like including cells in a vicinity of the fiber, dissolving and removing the fiber, and then coating a void with the blood vessel endothelial cells. However, because this method does not allow a fine (100 μm or less) opening diameter control of the fiber, it is difficult to construct a small blood vessel (arteriole-capillary-venule) of 100 μm or less.

Non-patent literature 2 discloses a method of constructing a three-dimensional tissue having a blood vessel network by producing a microchannel in collagen gel and culturing a cell sheet having a capillary structure on the gel. In this method, the blood vessel endothelial cells migrate and make a connection with the microchannel, thereby enabling circulation of a solution. However, the construction of the blood vessel network structure depends on self-organization of the cells, and thus it is difficult to control its three-dimensional configuration.

Patent literature 2 discloses a three-dimensional tissue body and a method of producing the same. The three-dimensional tissue body, in which cells are three-dimensionally arranged via an extracellular matrix, has at least one opening structure on its surface and a branched tubular structure that is communicated with the opening structure in its inside. However, similar to Patent literature 1, because the tubular structure in Patent literature 2 is also formed by self-organization of the cells as a driving force, it is difficult to control a three-dimensional configuration of the blood vessel network.

CITATION LIST

Patent Literature

PATENT LITERATURE 1: JP-A-2012-115254
PATENT LITERATURE 2: JP-A-2015-100334
Non-Patent Literature
NON-PATENT LITERATURE 1: Nat Mater. 2012 September; 11(9): 768-774
NON-PATENT LITERATURE 2: SCIENTIFIC REPORTS; 3: 1316

SUMMARY OF INVENTION

Problem to be Solved

The problem to be solved by the present invention is, for example, to provide a three-dimensional tissue that includes a vascular system (a blood vessel network and/or a lymphatic vessel network) having a desired structure and thickness, and a method of producing the three-dimensional tissue.

Means to Solve the Problem

The present inventors conducted extensive studies to solve the above problem, and found that gel such as gellan gum (GG) can be dissolved by incubating in a cationic solution, thereby completed the present invention. Accordingly, the present invention provides the followings:
(1) A method of producing a three-dimensional tissue having a vascular system structure, wherein the method comprises:
(a) a step of producing a template of a vascular system structure using a gel;
(b) a step of forming a three-dimensional tissue in a vicinity of the template;
(c) a step of dissolving the template using a cationic solution; and
(d) a step of seeding at least one of a blood vessel endothelial cell or a lymphatic vessel endothelial cell in a void remaining after the dissolution of the template.
(2) The method described in (1), in which a smooth muscle cell is seeded on the template in the step (b), or a smooth muscle cell is seeded before seeding at least one of the blood vessel endothelial cell or the lymphatic vessel endothelial cell in the step (d).
(3) A method of producing a three-dimensional tissue having a vascular system structure, wherein the method comprises:
(i) a step of producing a template of a vascular system structure using a gel;
(ii) a step of seeding at least one of a blood vessel endothelial cell or a lymphatic vessel endothelial cell on the template;
(iii) a step of forming a three-dimensional tissue in a vicinity of the seeded cell; and
(iv) a step of dissolving the template using a cationic solution.
(4) The method described in (3), in which a smooth muscle cell is further seeded after seeding at least one of the blood vessel endothelial cell or the lymphatic vessel endothelial cell in the step (ii).

(5) The method described in any one of (1) to (4), in which the gel is selected from a gellan gum (GG) gel, an alginic acid gel, a polyacrylic acid gel, a polyglutamic acid gel, a polyaspartic acid gel, and combinations thereof.
(6) The method described in any one of (1) to (5), in which the cationic solution is a tris-hydrochloric acid buffer solution, a tris-maleic acid buffer solution, a bis-tris buffer solution, or ethanolamine.
(7) The method described in any one of (1) to (6), in which a concentration of the cationic solution is 10 to 100 mM.
(8) The method described in any one of (1) to (7), in which the template is dissolved at 37° C. in the step (c) or (iv).
(9) A three-dimensional tissue including gel having a vascular system structure.
(10) The three-dimensional tissue described in (9), in which the gel is selected from gellan a gum (GG) gel, an alginic acid gel, a polyacrylic acid gel, a polyglutamic acid gel, a polyaspartic acid gel, and combinations thereof.

The present invention further provides the followings:
(11) The method described in any one of (1) to (10), in which pH of the cationic solution is 6.0 to 8.0.
(12) The method described in (11), in which the pH of the cationic solution is 7.4.
(13) The method described in any one of (1) to (12), in which the template is dissolved while shaking in the step (c) or (iv).
(14) The method described in (3) or (4) including a step (v) of coating a scaffold protein on the template after the step (i).
(15) The method described in claim 14), in which the scaffold protein is selected from the group consisting of a collagen, a laminin, a fibronectin, and combinations thereof.
(16) The method described in (3) or (4), in which the gel is modified with a cell adhesive peptide.
(17) A method of a producing a three-dimensional tissue that includes gel having a vascular system structure, wherein the method comprises:
(a) a step of producing a template of a vascular system structure using a gel; and
(b) a step of forming a three-dimensional tissue in a vicinity of the template.
(18) A method of producing a three-dimensional tissue that includes gel having a vascular system structure, wherein the method comprises:
(i) a step of producing a template of a vascular system structure using a gel;
(ii) a step of seeding at least one of a blood vessel endothelial cell or a lymphatic vessel endothelial cell on the template; and
(iii) a step of forming a three-dimensional tissue in a vicinity of the seeded cell.
(19) The method described in (17) or (18), in which the gel is gellan gum (GG) gel.

Effects of Invention

According to the present invention, the blood vessel network and/or the lymphatic vessel network having a desired opening diameter, length, and branch structure can be constructed inside the three-dimensional tissue body by using the template formed of the gel.

BRIEF DESCRIPTION OF DRAWINGS

FIG. 1 is a diagram illustrating results of dissolution of GG gel using five different solutions. (a) circle: 50 mM tris-hydrochloric acid buffer solution (pH7.4) (Tris-HCl), diamond: Dulbecco's modified eagle's medium (DMEM), square: phosphate buffered saline (PBS). (b) square: 50 mM tris-hydrochloric acid buffer solution (pH7.4) (Tris-HCl), triangle: 50 mM ethanolamine (MEA), circle: 50 mM HEPES buffer solution (HEPES Na). The gel was incubated for 180 minutes, and a residual weight of the gel was quantified at predetermined time points.

FIG. 2 is a diagram illustrating a relationship between dissolution of the GG gel and temperature. The gel was immersed in 50 mM tris-hydrochloric acid buffer solution (pH7.4), and time required for dissolution was measured. Open circle: room temperature, filled circle: 37° C.

FIG. 3 is a diagram illustrating cell patterning formed after removing the gel. Schematic diagrams of procedures of the patterning are shown in (a), and photo images of each procedure are shown in (b).

FIG. 4 is a diagram illustrating how a void is produced inside a three-dimensional tissue body. Schematic diagrams of production procedures of the void are shown in (a), and results of HE staining are shown in (b).

FIG. 5 is a diagram illustrating results of the test in which a blood vessel endothelial cell is adhered to an inner void generated by using a gellan gum (GG) gel.

FIG. 6 is a diagram illustrating results of the test in which human whole blood is circulated using a tube partially coated with HUVEC.

DESCRIPTION OF EMBODIMENTS

A first aspect of the present invention relates to a method of producing a three-dimensional tissue having a vascular system structure, which comprises:
(a) a step of producing a template of a vascular system structure using a gel;
(b) a step of forming a three-dimensional tissue in a vicinity of the template;
(c) a step of dissolving the template using a cationic solution; and
(d) a step of seeding at least one of a blood vessel endothelial cell or a lymphatic vessel endothelial cell in a void remaining after the dissolution of the template.

In one embodiment, a step of seeding a smooth muscle cell on the template is included in the step (b). In another embodiment, a step of seeding a smooth muscle cell before seeding at least one of the blood vessel endothelial cell or the lymphatic vessel endothelial cell is included in the step (d).

Another aspect of the present invention relates to a method of producing a three-dimensional tissue having a vascular system structure, which comprises:
(i) a step of producing a template of a vascular system structure using a gel;
(ii) a step of seeding at least one of a blood vessel endothelial cell or a lymphatic vessel endothelial cell on the template;
(iii) a step of forming a three-dimensional tissue in a vicinity of the seeded cell; and
(iv) a step of dissolving the template using a cationic solution.

In one embodiment, a smooth muscle cell is further seeded after seeding at least one of the blood vessel endothelial cell or the lymphatic vessel endothelial cell in the step (ii).

The term "vascular system" refers to an assembly of organs circulating blood and lymph throughout the body. When used in the present specification, the term "vascular system" specifically refers to a blood vessel system or a lymphatic vessel system. The blood vessel system includes an artery that carries blood sent out from the heart to all parts of the body, a capillary that supplies oxygen and a nutrient to a tissue and cell in a distal portion of the body and receives carbon dioxide and a waste product from the tissue and cell, and a vein that sends back the blood from the capillary to the heart. A thickness of the capillary is about 5 to 10 μm. A lymphatic vessel is a thin tube that begins with blind ending in a tissue and stores a tissue fluid. The beginning of the lymphatic vessel is referred to as a lymphatic capillary. The lymphatic capillaries are joined together to become gradually thicker and eventually merged into a venous system. When used in the present specification, the term "vascular system structure" refers to a network structure, such as a blood vessel network and a lymphatic vessel network, in a living tissue.

When used in the present specification, the term "three-dimensional tissue" refers to a three-dimensional assembly including at least one kind of cells. Such a three-dimensional tissue includes, though not limited to, a living tissue such as a skin, a hair, a bone, a cartilage, a tooth, a cornea, a blood vessel, a lymphatic vessel, a heart, a liver, a pancreas, a nerve, and an esophagus, and a solid cancer model (e.g., stomach cancer, esophagus cancer, colorectal cancer, colon cancer, rectum cancer, pancreatic cancer, breast cancer, ovarian cancer, prostate cancer, renal cell carcinoma, liver cancer).

As the "gel" used in the present invention, any substance that can be gelified by addition of ions, temperature change, or the like can be used after gelification, so long as it does not adversely influence cell growth and formation of the three-dimensional tissue. Examples of such gel includes, though not limited to, gellan gum (GG) gel, alginic acid gel, polyacrylic acid gel, polyglutamic acid gel, and polyaspartic acid gel. One kind of the gel may be solely used, or plural kinds of the gels may be used in combination. In a preferred embodiment, the gel used in the present invention is the GG gel.

Gellan gum (GG) is a natural linear polymer polysaccharide, extracellularly produced by Pseudomonas elodea using glucose or the like as a carbon source. GG forms gel that exhibits transparency, thermal resistance, and acid resistance in the presence of a monovalent or divalent metal salt. GG is available in two forms, HA gellan gum with high acyl group content and LA gellan gum from which the acyl group is removed. Either form may be used in the method of the present invention. Alternatively, both forms of GG may be used in combination. GG is commercially available, for example, as Nanogel (registered trademark)-TC, Grovgel, AppliedGel, Phytagel (trademark), or Gelrite. Gellan gum used in the present invention is not particularly limited as long as it is dissolved in a cationic solution described below.

The gel used in the present invention may be obtained by adding a monovalent or divalent cation to a substance that can be gelified by addition of ions for gelification. Examples of such a cation includes, though not limited to, a sodium ion, a calcium ion, a barium ion, and a magnesium ion. Alternatively, the gel may be obtained by cooling a solution having a high concentration (2 wt % or more) of the substance that can be gelified by addition of ions, and gelifying the substance.

As the "cationic solution" used in the present invention, any solution having positive charge may be used as long as it dissolves the template without adversely influencing the cell growth and the formation of the three-dimensional tissue. Examples of the cationic solution includes, though not limited to, a tris-hydrochloric acid buffer solution, a tris-maleic acid buffer solution, a bis-tris buffer solution, or ethanolamine. In a preferred embodiment, the cationic solution used in the present invention is the tris-hydrochloric acid buffer solution or ethanolamine.

No particular limitation is imposed on a concentration of the cationic solution as long as the template is dissolved without adverse influence on the cell growth and the formation of the three-dimensional tissue. In a preferred embodiment, the concentration of the cationic solution used in the present invention is about 1 to about 100 mM. For example, the concentration of the cationic solution used in the present invention is about 1 to about 100 mM, about 10 to about 100 mM, about 10 to about 90 mM, about 10 to about 80 mM, about 10 to about 70 mM, about 10 to about 60 mM, about 10 to about 50 mM, about 10 to about 40 mM, about 10 to about 30 mM, or about 10 to about 20 mM. In a more preferred embodiment, the concentration of the cationic solution used in the present invention is about 10 to about 50 mM.

No particular limitation is imposed on pH of the cationic solution as long as the template is dissolved, without adverse influence on the cell growth and the formation of the three-dimensional tissue. In a preferred embodiment, the pH of the cationic solution used in the present invention is about 6.0 to about 8.0. For example, the pH of the cationic solution used in the present invention is about 7.0, about 7.1, about 7.2, about 7.3, about 7.4, about 7.5, about 7.6, about 7.7, about 7.8, about 7.9, or about 8.0. In a more preferred embodiment, the pH of the cationic buffer solution used in the present invention is about 7.2 to about 7.6. In a further preferred embodiment, the pH of the cationic buffer solution used in the present invention is about 7.4.

The production method of the template in the step (a) or (i) is not particularly limited. For example, the template having a desired diameter, length, and branch structure may be manually or automatically formed using a micro pipette, a micro dispenser, a syringe, and the like. Further, an ink jet printer may be used. Alternatively, the template may be formed by producing a form having a desired size and shape and pouring the gel into the form for solidifying the gel.

In the step (b) or (iii), the three-dimensional tissue can be formed using a method known to those skilled in the art. For example, the three-dimensional tissue can be formed in accordance with production methods of the three-dimensional tissue disclosed in JP-A-2007-228921, JP-A-2012-115254, JP-A-2014-057527, or JP-A-2015-100334. Alternatively, the three-dimensional tissue may be formed by using a mixture obtained by mixing gel such as gel of an extracellular matrix (collagen, etc.) or the like and cells. In such a case, for example, research grade collagen (e.g., the one manufactured by Nippi. Inc.), Matrigel (registered trademark), or the like may be used.

A shape of the three-dimensional tissue formed in the step (b) or (iii) is not particularly limited and the three-dimensional tissue may be formed in various shapes, such as a linear shape, a sheet shape, and a shape of a three-dimensional cell assembly. In the present specification, the three-dimensional cell assembly refers to a cell assembly including a plurality of cell layers or a grown material of such a cell assembly.

The template and the three-dimensional tissue are formed on an appropriate substrate. Examples of the substrate include a culture container used for cell culturing and the like. The culture container may have a material and shape normally used for culturing cells and microorganisms. Examples of the material of the culture container includes, though not limited to, glass, stainless steel, plastic, and the like. Examples of the culture container includes, though not limited to, a dish, a cell culture insert (e.g., a Transwell (registered trademark) insert, a Netwell (registered trademark) insert, a Falcon (registered trademark) cell culture insert, a Millicell (registered trademark) cell culture insert, etc.), a tube, a flask, a bottle, a plate, and the like. In one embodiment, the template is produced on the culture container, and the three-dimensional tissue is directly formed in a vicinity of the template. In another embodiment, the template is produced on the appropriate substrate, and the template thus produced is arranged in the culture container. Then, the three-dimensional tissue is formed in a vicinity of the template.

In one embodiment, the template is dissolved by immersing the template together with the formed three-dimensional tissue in the cationic solution in the step (c) or (iv). In such a case, the cationic solution may be replaced at a predetermined time interval. In another embodiment, the template is dissolved by pouring the cationic solution over the formed three-dimensional tissue. In this manner, the template can be dissolved with little to no damage to the cells. In another embodiment, the three-dimensional tissue is incubated in the cationic solution for several hours to several days to dissolve the template. Incubation time may vary depending on the size or the like of the three-dimensional tissue and the template; however, the incubation is performed, for example, about 1 to about 48 hours, about 1 to about 36 hours, about 1 to about 24 hours, preferably about 1, about 2, about 3, about 4, about 5, about 6, about 7, about 8, about 9, about 10, about 11, about 12, about 13, about 14, about 15, about 16, about 17, about 18, about 19, or about 20 hours.

In one embodiment, the template is dissolved at about 10 to about 40° C. For example, the template is dissolved at about 10, about 15, about 20, about 25, about 30, about 31, about 32, about 33, about 34, about 35, about 36, about 37, about 38, about 39, or about 40° C. In a preferred embodiment, the template is dissolved at about 25 to about 37° C. In a more preferred embodiment, the template is dissolved at about 37° C. In another embodiment, the template is dissolved while shaking.

In one embodiment; a step (v) of coating a scaffold protein on the template may be included after the step (i). This can improve adhesion of the seeded cells to the template. Examples of the scaffold protein includes, though not limited to, collagen, laminin, fibronectin, a modified product thereof, a variant thereof, and a fragment thereof. One kind of the scaffold protein may be solely used, or plural kinds of the scaffold proteins may be used in combination.

In another embodiment, the gel is modified by a cell adhesive peptide. This can improve adhesion of the seeded cells to the template.

The cell used for forming the three-dimensional tissue in the method of the present invention is not partially limited, but examples thereof includes the one derived from an animal, such as a human, a monkey, a dog, a cat, a rabbit, a pig, a cow, a mouse, and a rat. A site from which the cell is derived is not particularly limited, and the cell may be a somatic cell derived from a bone, a muscle, an internal organ, a nerve, a brain, a skin, a blood, and the like and a germline cell. Such a cell may be an induced pluripotent stem cell (iPS cell) and an embryonic stem cell (ES cell). Alternatively, the cell may be a cultured cell such as a primary cultured cell, a sub-cultured cell, and a cell-line cell. Examples of the cell used for forming the three-dimensional tissue in the method of the present invention includes, though not limited to, a fibroblast, a cancer cell such as a liver cancer cell, an epithelial cell, a nerve cell, a dendritic cell, a cardiac muscle cell, a liver cell, an islet cell, a tissue stem cell, an immune cell, a blood vessel endothelial cell, a lymphatic vessel endothelial cell, and a smooth muscle cell. One kind of the cell may be solely used, or plural kinds of the cells may be used.

The cell can be seeded by a method generally performed in a field of cell biology. For example, seeding can be performed by injecting a medium containing the appropriate number of the cells into the void in the step (d). For example, seeding can be performed by adding a medium containing the appropriate number of the cells on the template in the step (ii).

According to the above-mentioned method of the present invention, it becomes possible to construct a gel network having an opening diameter of 100 μm or less, thereby making it possible to construct a blood vessel network and/or a lymphatic vessel network having an opening diameter of 100 μm or less. Further, a network can be produced by connecting a medium blood vessel, thick enough to be connected to an external tube, to arteriole-capillary-venule-medium blood vessel, and thus a liquid can be fed to the three-dimensional tissue from the outside via the external tube. Further, since the blood vessel network and/or the lymphatic vessel network having a desired opening diameter, length, and branch structure can be constructed, the three-dimensional tissue of large size (1 cm or more) can be constructed in vitro.

Another aspect of the present invention relates to a three-dimensional tissue including gel having a vascular system structure. Such a three-dimensional tissue is an intermediate of the three-dimensional tissue having a vascular system structure produced in the above-mentioned method of the present invention. In one embodiment, the gel is selected from a gellan gum (GG) gel, an alginic acid gel, a polyacrylic acid gel, a polyglutamic acid gel, a polyaspartic acid gel, and combinations thereof. In a preferred embodiment, the gel is the GG gel.

Another aspect of the present invention relates to a method of producing a three-dimensional tissue including gel having a vascular system structure, which comprises:
(a) a step of producing a template of a vascular system structure using a gel; and
(b) a step of forming a three-dimensional tissue in a vicinity of the template.

Another aspect of the present invention relates to a method of producing a three-dimensional tissue including gel having a vascular system structure, which comprises:
(i) a step of producing a template of a vascular system structure using a gel;
(ii) a step of seeding at least one of a blood vessel endothelial cell or a lymphatic vessel endothelial cell on the template; and
(iii) a step of forming a three-dimensional tissue in a vicinity of the seeded cell.

In one embodiment, in the method of producing the three-dimensional tissue including the gel having the vascular system structure described above, the gel is selected from a gellan gum (GG) gel, an alginic acid gel, a polyacrylic acid gel, a polyglutamic acid gel, a polyaspartic acid gel, and combinations thereof. In a preferred embodiment, the gel is the GG gel.

Another aspect of the present invention provides a kit for performing the above-mentioned method of the present invention, the kit including at least one reagent selected from the cell, the gel (or any substance that can be gelified), or the cationic solution described above. Each of these reagents is usually placed in an appropriate container and provided. Such a kit may include an appropriate reagent for facilitating the implementation of the above-mentioned method of the present invention, such as, for example, a diluting liquid, a buffer, and a rinsing reagent. Further, the kit may include an appropriate culture container, such as a dish, a cell culture insert, a tube, a flask, a bottle, and a plate, a micro pipette, a micro dispenser, a syringe, and the like. Further, the kit may include a material such as a manual necessary for performing the method of the present invention.

It should be understood that, unless particularly stated otherwise, the terms used in the present specification are used in the meanings as conventionally used in the art. Accordingly, unless otherwise defined, all technical terms and scientific technical terms that are used in the present specification have the same meanings as that commonly understood by those skilled in the art to which the present invention pertains. The term "about" varies to some extent in accordance with a context in which the word appears as understood by those skilled in the art. The term "about" means a numerical value in a range of typically ±10%, more typically ±5%, more typically ±4%, more typically ±3%, more typically ±2%, further more typically ±1%, of a numerical value to which the term is attached.

The present invention will be described in a detailed and specific manner below by way of Examples; however, Examples do not limit the scope of the present invention.

EXAMPLE

Example 1

Dissolution of GG Gel

It was verified whether the GG gel was dissolved using 50 mM tris-hydrochloric acid buffer solution (pH7.4) (Tris-HCl), Dulbecco's modified eagle's medium (DMEM), phosphate buffered saline (PBS), 50 mM ethanolamine (MEA), and 50 mM HEPES buffer solution (HEPES Na). To 25 mL of 0.5 w/t % GG solution (KELCOGEL-AFT available from SANSHO Co., Ltd.), 10 µL of 5 M calcium chloride solution was added at 90° C., and then the mixture was cooled. One hundred mg of the obtained gel was immersed in 20 mL of each of the above 5 solutions at 37° C. and a residual weight of the gel was quantified at predetermined time points.

Results are shown in FIG. 1. After 180 minutes of observation, the GG gel was dissolved in Tris-HCl and MEA.

Example 2

Relationship Between Dissolution of GG Gel and Temperature

It was verified whether the GG gel was dissolved using the tris-hydrochloric acid buffer solution. To 25 mL of 0.5 w/t % GG solution, 10 µL of 5 M calcium chloride solution was added at 90° C., and then the mixture was cooled. The obtained gel was immersed in 20 mL of 50 mM tris-hydrochloric acid buffer solution (pH7.4) at a room temperature or 37° C. and time required for dissolution was measured. An amount of the gel in use was 200 mg, 400 mg, and 600 mg.

Results are shown in FIG. 2. The time required for dissolution was decreased as the temperature increased.

Example 3

Cell Patterning Formed by Gel Removal

To 25 mL of 0.5 w/t % GG solution, 10 µL of 5 M calcium chloride solution was added at 90° C., and then the mixture was cooled to 40° C. The GG solution was dropped onto a dish at room temperature or an ice-cold dish to instantly form the gel. To each dish, 1×106 normal human dermal fibroblasts (NHDF) were seeded, and Dulbecco's modified eagle's medium (DMEM) containing 10% fetal bovine serum (FBS) was added. The dish was left to stand in a CO2 incubator (37° C., 5% CO2) for 24 hours to culture the cells in a vicinity of the gel. After the culture, DMEM was replaced with 20 mL of 50 mM tris-hydrochloric acid buffer solution (pH7.4), and the dish was left to stand for 3 hours.

Results are shown in FIG. 3. Schematic diagrams of procedures of the present Example are shown in (a), and photo images of each procedure are shown in (b). The GG gel was dissolved and removed by adding the tris-hydrochloric acid buffer solution, and the cells adhered to a vicinity of a region where the gel existed formed a pattern.

Example 4

Generation of Void in Inside of Three-Dimensional Tissue Body

To 25 mL of 0.5 w/t % GG solution, 10 µL of 5 M calcium chloride solution was added at 90° C., and then the mixture was cooled to 40° C. The GG solution was dropped into a 24-well cell culture insert at 50° C. to produce gel having a columnar shape. A three-dimensional tissue was formed in a vicinity of the gel using 1×106 NHDF with a method described in JP-A-2012-115254. Fibronectin (FN) and gelatin (G) were used to coat NHDF. After replacing DMEM with 70 mL of 50 mM tris-hydrochloric acid buffer solution (pH7.4), the cell culture insert was left to stand for 24 hours. In this manner, the GG gel was dissolved and removed. The tissue thus obtained was collected and a paraffin embedded slice of the tissue was produced. The paraffin embedded slice was produced in accordance with a known method. The slice thus produced was subjected t Hematoxylin-Eosin staining (HE staining). The HE staining was performed in accordance with a known method.

Results are shown in FIG. 4. Schematic diagrams of procedures of the present Example are shown in (a), and results of the HE staining are shown in (b). As shown in (b), a space obtained by removal of the template gel was observed in a vicinity of the center of the tissue.

Example 5

Adhesion Test of Blood Vessel Endothelial Cell to Inner Void

The gellan gum (GG) gel having a diameter of 500 µm and a length of 1 cm was arranged on 10 wt % gelatin gel (crosslinked by transglutaminase) with a size of 1 cm×1.5 cm×2 mm. A gelatin solution was added thereon to produce gel of the same size by crosslinking with transglutaminase (5 hour-incubation at 4° C.). The whole product was immersed in 35 mL of 50 mM tris-hydrochloric acid buffer solution (pH7.4) (Tris-HCl) at 37° C. for 12 hours to dissolve and remove the GG gel. In this manner, the gelatin gel having a tube structure was produced. About 50 µL of 0.2 mg/mL fibronectin (FN)/Tris-HCl solution was injected into the tube thus formed by connecting a PEEK tube (manufactured by AS ONE Corp.) to it. Then, the product was incubated for about 2 days in an incubator. About 50 µL of human umbilical vein endothelial cells (HUVEC) in a concentration of about 5×106 cells/mL were fluorescently labeled with CellTracker Green (manufactured by Thermo Fisher Scientific Inc.) and injected. Then, the cells were cultured for about 1 day in an incubator. A condition of adhesion was observed using the Olympus MVX10 microscope (connected with the Olympus DP80 camera). A circulation flow velocity at the time of injection was 3 cm/sec (about 100 times higher than a blood flow velocity in a human capillary) and a circulation flow rate was 0.36 mL/min.

Results are shown in FIG. 5. FN could be coated in the inner void of the tube generated by dissolving and removing the GG gel. Further, the blood vessel endothelial cell could be adhered to the inner void of the tube coated with FN.

Example 6

Circulation Test of Human Whole Blood

About 5 mL of whole blood was collected from a healthy 24-year old volunteer using a spitz tube containing heparin. Gelatin gel having a tube structure partially coated with HUVEC was produced in accordance with the method described in Example 5. The tube thus produced was connected to a PEEK tube (outer diameter of 700 μm, manufactured by AS ONE Corp.) and a silicon tube (inner diameter of 500 μm, manufactured by AS ONE Corp.), and the blood was circulated using a gear pump (manufactured by Immatek Corp.). A circulation flow velocity was 3 cm/sec, and a circulation flow rate was 0.36 mL/min. A circulation state was observed using the Olympus MVX10 microscope (connected with the Olympus DP80 camera).

Results are shown in FIG. 6. The human whole blood could be circulated inside the tube generated by dissolving and removing the GG gel.

INDUSTRIAL APPLICABILITY

The present invention is useful in a regenerative medical field. Further, the present invention is also useful in developing pharmaceuticals.

The invention claimed is:

1. A method of producing a three-dimensional tissue having a vascular system structure, the method comprising:
    producing a vascular system structure template made of a gel;
    forming a three-dimensional tissue in a vicinity of the vascular system structure template made of the gel;
    dissolving the vascular system structure template by a cationic solution; and
    seeding at least one of a blood vessel endothelial cell and a lymphatic vessel endothelial cell in a void remaining after the vascular system structure template is dissolved,
    wherein the gel comprises a gellan gum gel, and
    the cationic solution comprises a tris-hydrochloric acid buffer solution, a tris-maleic acid buffer solution, or a bis-tris buffer solution.

2. The method according to claim 1, wherein a concentration of the cationic solution is 10 to 100 mM.

3. The method according to claim 1, wherein the vascular system structure template is dissolved at 37° C.

4. The method according to claim 1, further comprising:
    seeding a smooth muscle cell before the seeding of at least one of the blood vessel endothelial cell and the lymphatic vessel endothelial cell.

5. The method according to claim 1, wherein the cationic solution comprises a tris-hydrochloric acid buffer solution.

6. The method according to claim 1, wherein the forming of the three-dimensional tissue includes seeding a smooth muscle cell on the vascular system structure template.

7. The method according to claim 6, wherein the seeding includes seeding the blood vessel endothelial cell and the lymphatic vessel endothelial cell.

8. The method according to claim 1, wherein the seeding includes seeding the blood vessel endothelial cell.

9. The method according to claim 8, further comprising:
    seeding a smooth muscle cell before the seeding of the blood vessel endothelial cell.

10. The method according to claim 1, wherein the seeding includes seeding the lymphatic vessel endothelial cell.

11. The method according to claim 10, further comprising:
    seeding a smooth muscle cell before the seeding of the lymphatic vessel endothelial cell.

12. The method according to claim 1, wherein the seeding includes seeding the blood vessel endothelial cell and the lymphatic vessel endothelial cell.

13. The method according to claim 12, further comprising:
    seeding a smooth muscle cell before the seeding of the blood vessel endothelial cell and the lymphatic vessel endothelial cell.

* * * * *